United States Patent [19]
DiPippo et al.

[11] Patent Number: 5,753,257
[45] Date of Patent: May 19, 1998

[54] BURN DRESSING

[75] Inventors: Ascanio DiPippo, Middletown, R.I.; William A. Lohse; Tom Ladas, both of Parsippany, N.J.

[73] Assignee: Water-Jel Technologies, Inc., Carlstadt, N.J.

[21] Appl. No.: 798,079

[22] Filed: Feb. 12, 1997

Related U.S. Application Data

[63] Continuation of Ser. No. 668,990, Jun. 21, 1996, abandoned, which is a continuation of Ser. No. 375,088, Jan. 19, 1995, Pat. No. 5,529,784, which is a continuation of Ser. No. 979,386, Nov. 19, 1992, Pat. No. 5,384,125, which is a continuation of Ser. No. 779,180, Oct. 18, 1991, abandoned, which is a continuation-in-part of Ser. No. 642,603, Jan. 17, 1991, abandoned, and Ser. No. 642,503, Jan. 17, 1991, abandoned.

[51] Int. Cl.$^6$ ............................................. A61F 13/00
[52] U.S. Cl. ........................ 424/443; 424/195.1; 424/447; 169/50
[58] Field of Search ............................. 424/443, 195.1, 424/447; 169/50

[56] References Cited

U.S. PATENT DOCUMENTS

| | | | |
|---|---|---|---|
| 3,902,559 | 9/1975 | Everingham | 169/50 |
| 4,265,233 | 5/1981 | Sugitachi | 128/156 |
| 4,552,138 | 11/1985 | Hofeditz | 128/156 |
| 4,784,842 | 11/1988 | London | 424/45 |
| 4,851,394 | 7/1989 | Kubodera | 514/54 |
| 4,931,282 | 6/1990 | Asmus | 424/448 |
| 4,997,425 | 3/1991 | Shioya | 604/304 |
| 5,009,890 | 4/1991 | DiPippo | 424/195.1 |

*Primary Examiner*—D. Gabrielle Phelan
*Attorney, Agent, or Firm*—Kenyon & Kenyon

[57] ABSTRACT

A burn dressing in the form of a non-irritating, non-woven synthetic fabric containing a therapeutic, nontoxic, water-soluble and biodegradable gel. The primary ingredients of the gel are water and Tea Tree Oil and/or Tea Tree Blend. A gum material or thickening agent is used to maintain the water and Tea Tree Oil and/or Blend in a thickened or gel state. Other ingredients are also provided for increasing shelf life and for imparting bacteriostatic and penetrating properties.

11 Claims, 1 Drawing Sheet

BURN DRESSING

This application is a continuation of application Ser. No. 08/668,990, filed on Jun. 21, 1996, now abandoned which is a continuation of application Ser. No. 08/375,088, filed on Jan. 19, 1995 now U.S. Pat. No. 5,529,784 which is a continuation of application Ser. No. 07/979,386, filed on Nov. 19, 1992, now U.S. Pat. No. 5,384,125 which is a continuation of Ser. No. 07/779,180, filed on Oct. 18, 1991, now abandoned, which is a continuation-in-part of Ser. No. 07/642,603, filed Jan. 17, 1991, now abandoned, and a continuation in part of Ser. No. 07/642,503, filed on Jan. 17, 1991, now abandoned.

BACKGROUND OF THE INVENTION

This invention relates to first aid devices for the care of burns and in particular, to a burn wound dressing that is useful for decreasing the temperature at the surface of a burn wound and to help prevent infection of the wound so as to help to lessen the extent of injury to a burn victim.

Numerous fire extinguishers and fire fighting devices are available. Of these, many of the fire extinguishers make use of asbestos cloth. Exemplary of such devices are those disclosed in U.S. Pat. No. 360,998 issued to J. W. Cloud on Apr. 12, 1887 and British Patent Specification No. 340,172 accepted on Dec. 24, 1930. However, it is now known that asbestos is a carcinogenic material and its use has fallen into disfavor throughout the world.

U.S. Pat. No. 3,902,559 issued to Everingham et al. on Sep. 2, 1975 also describes a fire fighting appliance. U.S. Pat. No. 3,902,559 describes a wool carrier of specified weave. The carrier is stored in a container with a viscous aqueous solution until needed. The solution contains a thickening agent and can contain Tea Tree Oil, RESI-GUARD and PHENONIP. The appliance can be worn by a fire fighter as protection from the fire.

Medicated pads and bandages for treatment of wounds, including burn wounds, are also well known. Exemplary pads and bandages are disclosed in U.S. Pat. Nos. 3,062,210, 3,089,492, 3,395,063, 3,624,224, 3,657,760, 3,750,666 and 4,310,509.

It can be disadvantageous to form a burn dressing from wool. Wool can include traces of impurities remaining from processing steps and it can be expensive to remove these impurities from the wool to assure cleanliness and sterility. U.S. Pat. No. 4,306,551 refers to an adhesive bandage having a substrate with a matrix having a synthetic resin with a liquid emulsion consisting of carbohydrate or protein incorporated therein. The bandage can be sterilized by irradiation and still retain its tackiness.

With respect to the care of burns, the main objectives are to relieve pain, help prevent contamination, eliminate the source of heat and stop the burn progression. Dry dressings do not eliminate the heat source. In fact, dry dressings retain heat and cause the burn area to enlarge, thereby intensifying the severity of the injury. In addition, dry dressings provide little protection against contamination and pain and usually adhere to burnt clothing and skin tissue. A great deal of pain and skin damage can result from the removal of dry dressings.

Ordinary tap water has also been used in emergency situations, but it is not practical and only superficially eliminates the heat source. Furthermore, water does not rapidly penetrate through clothing or skin tissue. In addition, tap water does not provide protection against contamination and can even cause contamination. Tap water can also irritate exposed nerve endings causing intensified pain and discomfort. Finally, hypothermia can be induced by the use of tap water because water cools by uncontrolled evaporation.

It is therefore desirable to provide an improved burn dressing that has good bacteriostatic activity and that aids in the care of burn wounds.

SUMMARY OF THE INVENTION

Generally speaking, in accordance with the invention a burn dressing in the form of a synthetic non-woven fabric carrier impregnated with a thickened aqueous solution or water based gel is provided. The active ingredients of the solution are preferably Tea Tree Oil and/or Tea Tree Blend, bacteriostatic agents and water. The carrier is preferably a two-layer, non-woven polyester strip or patch and is preferably stored with the gel in a pocket size storage pouch. A thickening agent or gum material should be used to maintain the water and active ingredients in a thickened or gel state. Other ingredients can also be provided for increasing shelf life and for imparting additional bacteriostatic properties.

Accordingly, it is an object of the invention to provide an improved burn dressing.

Another object of the invention is to provide a burn care product that can be applied directly to a burn wound.

A further object of the invention is to provide a burn dressing that can be applied directly to a burn injury to promote healing of the injury.

Still other objects and advantages of the invention will in part be obvious and will in part be apparent from the specification.

The invention accordingly comprises a product possessing features, properties, and the relation of components and the several steps and the relation of one or more of such steps with respect to each of the others thereof, which will be exemplified in the product and method hereinafter described, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

A burn dressing in accordance with the invention is formed of a fabric carrier impregnated with a burn care gel or thickened solution for reducing heat and providing bacteriostatic properties. The fabric is preferably a non-woven synthetic material that will hold a substantial quantity of gel to apply an effective amount of gel to a burn wound to reduce heat and help prevent infection. The fabric should be capable of being sanitized by radiation and non-irritating to burned tissue. The gel should be therapeutic, non-toxic, bacteriostatic, water soluble and bio-degradable. It is preferable to include Tea Tree Oil or Tea Tree Blend in the gel.

An especially preferred fabric carrier for applying the burn care gel to a wound is formed of polyester, such as polyethylene terephthalate (PET), especially medical grade non-woven 100% polyester fabric. The fabric may also contain other synthetic fibers such as rayon and can include surface finishing agents. The polyester fabric can be formed into strips or patches having dimensions ranging from about 2"×2" to about 12"×20". The strips are preferably in a layered construction to promote gel retention between the layers. A fabric carrier constructed in accordance with a preferred embodiment of the invention can hold about 12 to 25 grams of gel per gram of carrier. The fabric strips can be combined with the burn treatment gel in pocket sized pouches to provide a convenient method for transporting the burn dressing. Measures should be undertaken throughout production to insure proper sanitization and the final product can be sterilized by appropriate radiation sterilization techniques.

Figure 1:
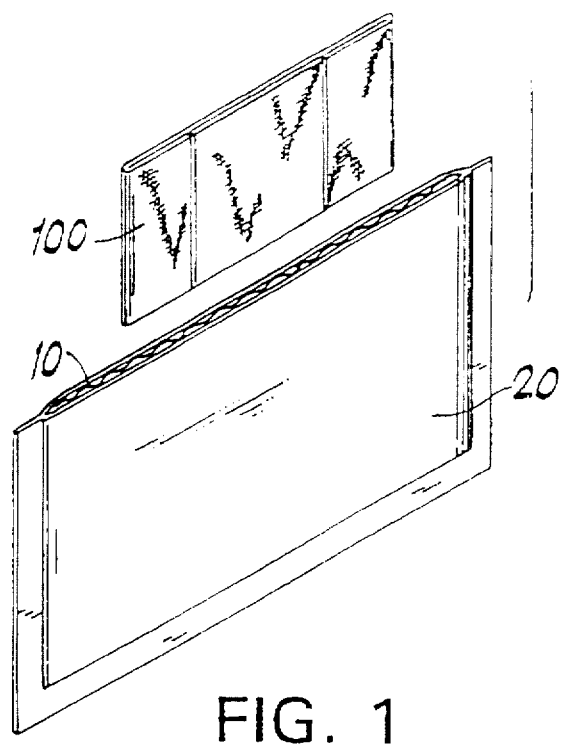
FIG. 1 is an exploded view of a burn dressing, in accordance with an embodiment of the invention, showing an opened storage pouch containing a thickened aqueous solution or gel and a folded fabric carrier.
Figure 2:
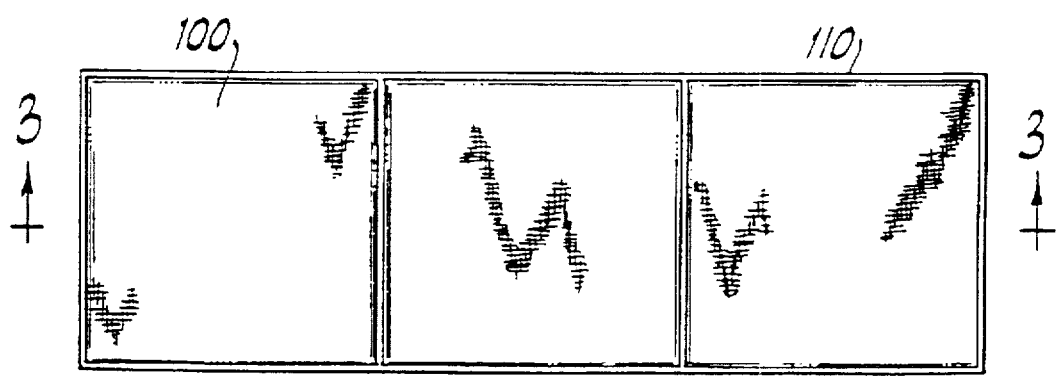
FIG. 2 is a top plan view of the non-woven fabric carrier of FIG. 1.
Figure 3:
FIG. 3 is a cross-sectional view of the fabric carrier of FIG. 2, taken along a line 3—3.

A non-woven fabric carrier 100 in accordance with one embodiment of the invention is shown in FIGS. 1, 2 and 3. FIG. 1 also shows a storage pouch containing a quantity of a gel or a thickened aqueous solution 10 for impregnating carrier 100. It is preferable to include an excess of gel or aqueous solution 10, beyond the absorbance capacity of carrier 100 in a storage pouch 20. Carrier 100 can be folded, as shown in FIG. 1, prior to insertion into pouch 20. FIG. 1 shows pouch 20 in the opened condition. Ordinarily, pouch 20 is sealed at all four sides.

FIGS. 2 and 3 show a plurality of heat sealed portions 110 of carrier 100. Heat sealed portions 110 provide a plurality of pouches 115 between the two layers of carrier 100. The embodiment shown in FIGS. 1, 2 and 3 are merely exemplary and other embodiments such as those having 2×2 square pouches, 2×3 square pouches and other configurations of the fabric carrier and pouch are also possible in accordance with the invention. Sealed portions 110 can also be sealed sonically.

It is preferable to include Tea Tree Oil in gel or solution 10. Tea Tree Oil is a natural oil obtained from Melaleuca Alternifolia, a tree that grows on the north coastal areas of the state of New South Wales and in southern Queensland, Australia. Principle active constituents of tea tree oil are 1-terpinen-4-O1, terpinolene, cineole, sesquiterpenes, p-cynene and pinene. Similar types of oils are obtained from allied species of Melaleuca such as *Melaleuca lineariifolia* and *Melaleuca leucadendron*.

A preferred material for a storage pouch such as pouch 20 has a three layer construction of a layer of polyester having a layer of aluminum thereon and a layer of Scotchpak® heat sealable polyester film 229 thereon. Scotchpak®-229 is available from the Specialty Film Products division of 3M of St. Paul Minn. The three layers are adhered with adhesive.

A burn care product prepared in accordance with an embodiment of the invention can include a thickened aqueous solution or a gel containing water and Tea Tree Oil and/or Tea Tree Blend sold by G. R. Davis Pty Ltd. of Hornby, Australia as its active ingredients. Other embodiments contain tea tree oil mixed with other anti-bacterial and preservative agents. Additional ingredients can include benzalkonium chloride, quaternary ammonium salts and the like. A gum material or thickening agent is used for forming the gel and/or keeping the ingredients dispersed evenly in the aqueous solution. Surfactants and oils, such as glycerine, can also be included to keep the dressing from drying and to improve the penetrating properties of the solution. Additional ingredients can be used to improve the shelf life and impart bacteriostatic properties.

In one preferred embodiment, ordinary tap water, purified water, U.S.P. grade purified water, sterile water, halogenated water, especially chlorinated water which is also known as bleach water or chloropactin and mixtures thereof are used. The water is used in an amount between about 80 and 98% by weight of the solution. In a more preferred embodiment, the amount of water is between about 90 and 97% by weight of the solution.

A gum can be used as a thickening agent to provide a solution or gel of increased viscosity. The function of the gum is to keep the water in place and to provide a gel. Many types of gums can be used. Suitable gums include, but are not limited to, xanthan gum, locust bean gum, guar gum and the like and mixtures thereof. Alginates, carrageenans and polyacrylamides can also be included. In one especially preferred embodiment of the invention, KELTROL® manufactured by Kelco Company of Clark, N.J. is used. KELTROL® is formed of 100% xanthan gum. The gum is used in an amount of between about 0.5 and 5% by weight. More preferably, the gum is used in an amount between about 0.5 and 3% by weight and most preferably, the gum is used in the amount of between about 0.6 and 1% by weight.

Alternatively, either KELGUM® or KELSET® can be used as all or part of the gum material. Both KELGUM® and KELSET® are manufactured by Kelco Company of Clark, N.J. KELGUM® is a 50:50 mixture of xanthan gum and locust bean gum and KELSET® is 100% calcium alginate, a gum-type material.

Other ingredients are also optionally included in the burn treatment product prepared in accordance with the invention. One such ingredient that can be used for providing smoothness and emollient properties is glycerin. Glycerin can be used either alone or in solution of sorbitol or other physiologically safe polyhydroxy compounds such as propylene glycol. Glycerin should be used in a maximum of up to about 5% by weight and preferably between about 0.5 and 3%. Most preferably, glycerin is used in an amount of about 1%.

A surfactant or surface active agent can be used in a quantity sufficient to maintain the emulsion. Preferred surfactants include octoxynol, nonoxynol, alkarylpolyglycol esters, cocoalkylomaide and amine neutralized tridecylbenzene sulphonates. In a preferred embodiment, the amount of surfactant is between about 0.07 and 0.25% by weight, preferably about 0.1%. Suitable surfactants include, but are not limited to, SURFAX 90® and octoxynol 9.

Additives such as Zephyrin chloride or other equivalent compounds can be used to control infection. Suitable equivalent compounds can include quaternary compounds such as benzalkonium compounds. Other additives such as picloxydine, octyphenoxy polyethoxyethanol and benzalkonium chloride are also desirable.

A liquid preservative such as PHENONIP® can also be included. PHENONIP® is a mixture of phenoxyethanol, methylparaben, lethylpareben, propylparaben and butylparaben. Such a preservative should be used in an amount between about 0.125 and 0.35% by weight, more preferably, between about 0.2 and 0.25%±0.01%.

Methylparaben is a bacteriostat and can be used as a preservative either with or without PHENONIP®. Such a preservative can be used in an amount between about 0.01 and 0.5%, more preferably about 0.25%.

In still another alternate embodiment, diazolidinyl urea or imidazolidinyl urea II is included as a preservative. Imidazolidinyl urea II is sold under the tradename GERMALL® II by Sutton Laboratories, Inc. It has the molecular formula $C_8H_{14}N_4O_7$ and the chemical name N-(Hydroxymethyl-N-(1,3-dihydroxymethyl-2,5-dioxo-4-imidazolidinyl-N'-hydroxymethyl) Urea.

GERMALL® II is a useful preservative because it has a wide spectrum of activity, particularly against troublesome house microorganisms. It is active against gram negative bacteria such as Pseudomonas as well as against yeast and mold. The urea is preferably used in an amount between 0.1 and 0.35%. It can be used alone or in combination with parabens.

Pre-mixed combinations of ingredients are also suitable. For example, GERMABEN® manufactured by Sutton Laboratories, Inc. can be used as a replacement for some or all of the parabens.

The gel or thickened aqueous solution can include Tea Tree Blend. Tea Tree Blend is a mixture of terpenes and terpinols that are generally naturally occurring, but can be synthetically 1 prepared. The terpene and terpinol compounds can be obtained either as pure compounds derived from the natural oils or as mixtures of components derived from plants of *Melaleuca alternifolia*, *Melaleuca lineariifolia*, *Melaleuca leucadendron*, *Eucalyptus longirostris* and closely related species. In a preferred embodiment, Tea Tree Blend is a blend of tea tree oil and certain distillate fractions of eucalyptus oil which provides a product having characteristics similar to those of tea tree oil and which can be used to extend the available supply of teat tree oil.

However, it has been discovered that a burn dressing prepared in accordance with the invention using Tea Tree Blend has enhanced bacteriostatic properties as compared with a similar burn dressing prepared using tea tree oil. Although Tea Tree Blend and tea tree oil are similar in many respects, Tea Tree Blend has a higher proportion of levo-rotary enantiomers. It is thought that it is these levo-rotary enantiomers that lead to the enhanced properties of a burn dressing prepared using Tea Tree Blend.

Tea Tree Blend has the following major constituents in the approximate percentages designated below, as determined by gas chromatography in combination with mass spectrometry. All percentages are by weight and can vary by up to about plus or minus 10%.

| | |
|---|---|
| α-p-mentha 1,5,diene | 0–35% |
| α-terpineol | 15–20% |
| terpinen-4-ol | 12–15% |
| 1,8,cineole | 7–14% |
| α-terpinene | 4% |
| p-cymeme | 3–7% |
| γ-terpinene | 3–7% |
| α-pinene | 2–6% |
| limonene | 1–5% |
| aromadendrene | 1% |
| terpinolene | 1–3% |
| myrcene | 0–1% |
| α-phellandrene | 0–14% |

The remainder of the Blend is made up of some or all of the following compounds, with no single compound being above about 1% of the Blend.

| | |
|---|---|
| β-pinene | humulene |
| camphene | γ-muurolene |
| camphor | α-muurolene |
| sabinene | viridiflorene |
| myrcene | piperitone |
| 1,4,cineole | piperitol |
| hexanol | α-cadinene |
| allyl hexanoate | nerol |
| p-α-dimethylstyrene | geraniol |
| α-cubebene | 8-p-cymenol |
| α-copaene | calamenene |
| α-gurjunene | α-eudesmol |
| linalool | β-eudesmol |
| 1-terpineol | australol |
| β-terpineol | traces of sesquiterpenes |
| β-elemene | caryophyllene |
| alloaromadendrene | |
| 4,10-dimethyl-7-isopropyl bicyclo(4,4,0)-1-4-decadiene | |

Since the Blend is not a natural oil, the variation in composition exhibited by natural oils can be minimized leading to standardization of burn treatment. However, some variation is still present, particularly in the minor constituents.

The physical constants of the Blend are generally as follows:

| | |
|---|---|
| Refractive index at 20° C. | between about 1.4743 and 1.4813 |
| Relative density at 20° C. | between about 0.890 and 0.910 |
| Optical rotation at 20° C. | between about −14° and −24° |
| Solubility in 85% ethanol (v/v) at 20° C. | soluble in less that an about 1.5 vols |
| General description | clear, colorless to pale yellow liquid, mobile at 20° C. |

Tea Tree Blend was tested for anti-bacterial activity against a variety of organisms and the following results were obtained form a 1:125 dilution of the Blend in water, a 1:250 dilution of the Blend in water and a reference standard:

| | 1:125 | 1:250 | Ref. stand |
|---|---|---|---|
| TIME 0 | | | |
| *Staphylococcus aureus* | $8.2 \times 10^5$ | $1.5 \times 10^6$ | $1.4 \times 10^6$ |
| *Escherichia coli* | $5.0 \times 10^1$ | $2.1 \times 10^3$ | $9.5 \times 10^5$ |
| *Pseudomonas aeruginosa* | <1.0 | $1.6 \times 10^6$ | $1.5 \times 10^6$ |
| *Pseudomonas vulgaris* | $6.0 \times 10^1$ | $1.0 \times 10^3$ | $7.4 \times 10^5$ |
| *Candida albicans* | $5.1 \times 10^4$ | $6.7 \times 10^4$ | $5.8 \times 10^4$ |
| *Aspergillus niger* | $3.0 \times 10^5$ | $7.5 \times 10^5$ | $7.5 \times 10^5$ |
| TIME 7 DAYS | | | |
| *Staphylococcus aureus* | <1.0 | <1.0 | <1.0 |
| *Escherichia coii* | <1.0 | <1.0 | $1.7 \times 10^6$ |
| *Pseudomonas aeruginosa* | <1.0 | $1.1 \times 10^7$ | $1.4 \times 10^6$ |
| *Pseudomonas vulgaris* | <1.0 | <1.0 | $2.8 \times 10^5$ |
| *Candida albicans* | <1.0 | <1.0 | $4.9 \times 10^4$ |
| *Aspergillus niger* | $5.5 \times 10^5$ | $4.5 \times 10^5$ | $4.5 \times 10^5$ |
| TIME 28 DAYS | | | |
| Staphylococcus | <1.0 | | <1.0 |
| *Escherichia coli* | <1.0 | | $9.1 \times 10^5$ |
| *Pseudomonas aeruginosa* | <1.0 | | $4.6 \times 10^5$ |
| *Pseudomonas vulgaris* | <1.0 | | $7.3 \times 10^5$ |
| *Candida albicans* | <1.0 | | $1.1 \times 10^5$ |
| *Asperillus niger* | $5.0 \times 10^4$ | | $4.5 \times 10^5$ |

It is believed that it is the interaction of the various compounds in the Tea Tree Blend that provides the anti-bacterial effect. Use of any of the compounds separately is not effective.

The Tea Tree Blend itself is flammable and Tea Tree Blend or tea tree oil should be used in an amount of less than about 20% of the burn treatment product. In an alternate embodiment of the invention, Tea Tree Blend is used in combination with tea tree oil and the total amount of Tea Tree Blend and/or tea, tree oil is between about 0.1% and 20%. In a more preferred embodiment, the Tea Tree Blend, tea tree oil or the mixture is used in an amount between about 0.1 and 5.0%, more preferably, between about 0.5 and 1.5%.

The following examples show the preparation of burn dressings prepared in accordance with the invention. These examples are presented for purposes of illustration only and are not intended to be construed in a limiting sense.

EXAMPLE 1

A particularly well suited gel has the following composition.

| Ingredients | Grade | % w/w |
|---|---|---|
| Glycerin | U.S.P. | 1.0 |
| Octoxynol 9 (TRITON X-100 ®) | N.P. | 0.1 |
| Tea Tree Oil, Natural | — | 0.5 |
| Propylene Glycol (and) Diazolidinyl Urea (and) Methylparaben (and) Propylparaben (GERMABEN II ®) | C.T.F.A. | 1.0 |
| Xanthan Gum (KELTROL 1000 ®) | N.F. | 1.0 |
| Purified Water | U.S.P. | 96.4 |
| Total | | 100 |

The glycerin, octoxynol 9, tea tree oil and GERMABEN II were combined in a pre-sanitized stainless steel container and mixed with a Lightnin Mixer. The xanthan gum was added and a smooth slurry was formed. The purified water was charged to a pre-sanitized batching tank equipped with a Lightnin Mixer and sidesweep agitation. During constant agitation, the slurry was incorporated and the ingredients were mixed for at least one hour to yield a homogeneous lump free gel product.

The gel had the following characteristics:

| | | |
|---|---|---|
| 1. Appearance | | A fluid but viscous off-white gel, having a characteristic odor. |
| 2. pH | | 4.5–7.0 |
| 3. Specific Gravity | 25° C./25° C. | 0.97–1.02 |
| 4. Viscosity (cps) Brookfield Model RVT, spindle size #3, speed 20 r.p.m. | | 1000–12000 |
| 5. Total Parabens (%) | 0.35 | Range: (Theoretical amount |
| | 0.315–0.385 | ± 10% of Theoretical) |
| 6. Diazolidinyl Urea (%) | 0.3 | Range: |
| | 0.23–0.33 | (Theoretical amount ± 10% of Theoretical) |
| 7. Microbiological Limits Test | | Less than 100 bacteria and less than 100 molds per gram of product |

The off-white, translucent, smooth viscous gel product was added to aluminum pouches containing dressing strips of non-woven Polyester Staple to yield a burn dressing product. Polyester Staple is a family of fiber products made from polyethylene terephthalate polymer. Polyester Staple is typically not irritating to human skin but will burn if exposed to flame. The pouches were then sealed and sterilized by gamma radiation at 1.10 Mrad (minimum) to 1.70 Mrad (maximum).

EXAMPLE 2

A particularly well suited carrier is formed of 100% polyester non-woven medical grade fabric and is available from the Veratec division of Hoechst Celanese Corporation, Charlotte, N.C. This fabric has approximately the same absorbtivity (about 12 to 25 grams of gel absorbed per square yard or gram of fabric) of the gel of Example 1 as does wool i.e., this fabric can hold the same quantity of gel as wool and can therefore provide similar burn care qualities. It has been determined that such fabric is particularly useful in providing an effective amount of gel without creating any problems associated with gel spillage and excessive gel retention in the carrier. This fabric is also shown to be suitable for contact with wound areas and is not irritating. The fabric is both sonically sealable and heat sealable and is preferably provided in a two layer structure with the two layers sealed at selected positions to form a plurality of sealed pouches. These pouches aid in holding gel and improve the burn care properties of the device.

The use of a non-woven synthetic carrier has advantages over natural wool. When wool is processed, impurities from wool treatment and processing remains in the fibers. These impurities vary, depending on the wool source. These impurities can react unfavorably with the burn treatment gel or with the burn wound. Accordingly, burdensome procedures must be employed to provide an acceptable wool carrier. Furthermore, it is desirable to sterilize the burn treatment product by radiation treatment. Synthetic fabrics are more suitable for such sterilization than are natural fabrics. Accordingly, a synthetic fabric carrier has advantages.

Two 2"×6" strips were sealed at the edges and twice cross-wise to yield three 2"×2" pouches such as is shown in FIG. 2. These strips had an initial weight of about 1.8 gm and could absorb about 33–36 gm of the gel described in Example 1 (about 18–20 grams gel per gram carrier). A 2"×2" single layer strip of this fabric will hold about 6 grams of gel; a 4"×4" strip had a fill volume of about 44.0 g±2.0 g; and a 4"×14" strip had a fill volume of about 127.0 g±2.0 g. This absorbtivity has been determined as being in the preferred optimum range of 12 to 25 of gel/g carrier as providing desired results without the disadvantages of insufficient or excessive absorbtivity.

Other tests were conducted and yielded the following absorbtivity data:

2"×6"—15.368 g/g and /or 2.21 g/sq. inch

4"×4"—14.574 g/g and /or 2.052 g/sq. inch

4"×14"—13.864 g/g and /or 1.802 g/sq. inch

The fabric used in this Example can be characterized as follows:

| PROPERTY/REQUIREMENT | SPECIFICATION & TOLERANCE |
|---|---|
| Cut Length, inches | 1.45 ± 0.10 |
| Denier filament | 1.38 ± 0.24 |
| Tenacity, g/dyne | 6.2 ± 1.0 |
| Elongation, % | 24.0 ± 15.1 |
| Crimp, % | 27.0 ± 4.5 |
| Crimp Frequency, crimps/inch | 12.5 ± 2.5 |
| Fiber openness | 9.2 ± 3.1 |
| Color L | 94.5 ± 1.7 |
| b | 1.2 ± 0.8 |
| Optical Brightener | None |
| TiO2, Ti Content, ppm | 1600 ± 200 |
| Moisture % | Target 0.4, Max |
| Finish Type | 12 |
| Finish, % | 0.13 ± 0.05 |
| Contamination - Splinters, per pound | 0 (30 max.) Free from all foreign matter and off-color fiber. |
| Sale weight, lb. | 775 + 25 |

| PROPERTY/REQUIREMENT | SPECIFICATION & TOLERANCE |
| --- | --- |
| Denier | – 50 Single |
| Weight (g/sq yd) | 68.9 |
| Thickness (mils) | 44.3 |
| Strip tensile (lb/in) | |
| MD | 27.7 |
| CD | 9.7 |
| Absorbency (water) | |
| Time (sec) | 60+ |
| Capacity (g/g) | 11.1 |

EXAMPLE 3

The gel of Example 1 was altered to increase the Xanthan Gum to 1.25% W/w and the purified water was decreased to 94.5% W/w. The resultant gel had increased viscosity and improved adherence to the carrier. The carrier was the 100% non-woven medical grade polyester fabric of Example 2.

EXAMPLE 4

360 ml of glycerin (12.2 oz), 719 ml of SURFAX 90® (24.2 oz), 360 ml of Tea Tree Blend (12.2 oz) and 719 ml of GERMABEN® (24.2 oz) were combined and mixed thoroughly. 719 g of KELTROL® (1.61 lbs) was gradually added with stirring. The resulting liquid mixture was added to 19.3 gallons of water and mixed thoroughly for about 15 minutes.

The product has a specific gravity of 0.968, a pH of 6.4 and remained a gel at temperatures of greater than about 110° F. The product had a viscosity as measured using a Brookfield #3 spindle at 20 rpm of 2250 cps. The product tested positive for a surfactant, xanthan gum, GERMABEN II®, glycerin, Tea Tree Blend and KELTROL® even after 5 freeze/thaw cycles. No colonies were observed using a microbiological Millipore test.

EXAMPLE 5

A gel was prepared as described in Example 4 except that 719 g of KELSET® was substituted for the KELTROL®.

The gel has a specific gravity of 0.99, a pH of 6.7 and remained a gel at temperatures of greater than about 110° F. The gel had a viscosity as measured using a Brookfield #3 spindle at 20 rpm of 2500 cps. The gel tested positive for a surfactant, xanthan gum, GERMABEN II®, glycerin, Tea Tree Blend and KELTROL® even after 5 freeze, thaw cycles. No colonies were observed using a microbiological Millipore test.

In general, an embodiment of the gel in accordance with the invention conforms to the following description:

| | |
| --- | --- |
| Appearance | A fluid but viscous off-white gel, having a characteristic odor. |
| pH | 4.5.–7.0 |
| Specific gravity 25° C./25° C. | 0.97–1.02 |
| Viscosity (cps) Brookfield Model RVT, Spindle size #3, Speed 20 rpm | 1000–12000 |
| Total parabens | Between about 0.315 and 0.385% |
| Diazolidinyl Urea (5) | Between about 0.27 and 0.33% |
| Microbiological limits test | Less than 100 Bacteria and less than 100 Molds per ml of product. |
| Stability | Over a wide temperature range. |

A gel formed in accordance with the invention is used by direct application to a burn wound. When the gel is provided with a carrier, the entire carrier can be used to cover the burn. Debridement of the wound prior to use of the burn treatment product is not necessary as the dressing will actually aid in such debridement.

The burn care solution of the invention rapidly penetrates through clothing and wets, cools and soothes a burn area. The burn area is wet, cooled and soothed not only on the surface, but also beneath the surface, thereby reducing progression of the area and the severity of the burn. The burn dressing cools by heat transference and helps to create an isothermic environment when severe and/or massive burns are involved. In addition, the burn dressing helps reduce the possibility of contamination by completely covering the burn wound and by helping to block out air-born bacteria. Clothing and skin tissue do not adhere to the burn dressing and when the dressing is removed, no additional pain or skin damage is caused.

The burn dressing provided in accordance with the invention is non-toxic, water soluble and retains its properties even after extended storage. It is suitable for use with any type of burn, including chemical burns. Furthermore, the method of using the product is easy and painless.

It will thus be seen that the objects set forth above, among those made apparent from the preceding description, are efficiently attained and, since certain changes may be made in the above product without departing from the spirit and the scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method for treating a burn wound comprising:
   removing a sterile shelf-stable pocket-sized burn dressing from a sealed pocket-sized package, the pocket-sized burn dressing being comprised of a non-woven synthetic carrier impregnated with a water based gel or thickened aqueous solution suitable for treatment of a skin burn, said water based gel or thickened aqueous solution being comprised of about 80–98% water and about 0.1–20% by weight Tea Tree oil, a bacteriostatic agent and gum or thickening agent, wherein the carrier is impregnated with at least about 1.8 grams of the water based gel or thickened aqueous solution per square inch of said carrier; and
   applying the burn dressing to a burn wound.

2. The method according to claim 1, wherein said gel or thickening agent produces a viscosity from about 1000 to about 12,000 cps as measured using a Brookfield #3 spindle at 20 rpm.

3. The method according to claim 1 wherein said gum or thickening agent is selected from the group consisting of xanthan gum, locust bean gum and guar gum.

4. The method according to claim 1 wherein said Tea Tree oil is used in an amount between about 0.5 and 1.5% by weight of said water based gel or thickened aqueous solution.

5. The method according to claim 1 wherein said water based gel or thickened aqueous solution includes a preservative component.

6. The method according to claim 5 wherein said preservative component includes diazolidinyl urea, methylparaben and propylparaben.

7. The method according to claim 1 wherein said water based gel or thickened aqueous solution includes glycerin and a surfactant.

8. The method according to claim 1 wherein said sealed pocket-sized package contains excess water based gel or thickened aqueous solution beyond the absorbance capacity of said carrier.

9. The method according to claim 1 wherein the water is used in an amount between about 80 and 98% by weight of said water based gel or thickened aqueous solution.

10. The method according to claim 1 wherein the water is used in an amount between about 90 and 97% by weight of said water based gel or thickened aqueous solution.

11. The method according to claim 1 wherein said sterilizing is by gamma radiation.

* * * * *